US012793835B2

(12) United States Patent
Zhou et al.

(10) Patent No.: US 12,793,835 B2
(45) Date of Patent: Nov. 10, 2026

(54) MEDICAL IMAGING METHOD AND MEDICAL IMAGING SYSTEM

(71) Applicant: GE Precision Healthcare LLC, Waukesha, WI (US)

(72) Inventors: Aizhen Zhou, Beijing (CN); Zhaohua Guo, Beijing (CN); Ziyi Yuan, Beijing (CN); Yan Wang, Beijing (CN); Yong Xu, Beijing (CN); Qingming Peng, Beijing (CN); Tingting Yue, Beijing (CN); Sai Kumar Pennujuru, Bengaluru (IN); Joseph Adamski-Smith, Waukesha, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 220 days.

(21) Appl. No.: 18/767,716

(22) Filed: Jul. 9, 2024

(65) Prior Publication Data

US 2025/0022576 A1 Jan. 16, 2025

(30) Foreign Application Priority Data

Jul. 14, 2023 (CN) ........................ 202310868958.1

(51) Int. Cl.
*G16H 30/20* (2018.01)
*G06T 7/00* (2017.01)
*G16H 30/40* (2018.01)

(52) U.S. Cl.
CPC ........... *G16H 30/20* (2018.01); *G06T 7/0012* (2013.01); *G16H 30/40* (2018.01); *G06T 2210/41* (2013.01)

(58) Field of Classification Search
CPC ...... G16H 30/20; G16H 30/40; G06T 7/0012; G06T 2210/41; A61B 6/465; A61B 6/5241; A61B 6/542; A61B 6/463; A61B 6/4411; A61B 6/4464; A61B 6/467; A61B 6/469
USPC ........................................................ 382/128
See application file for complete search history.

(56) References Cited

U.S. PATENT DOCUMENTS 10,098,598 B2 10/2018 Lee
2016/0361035 A1* 12/2016 Lee ...................... A61B 6/4452
2022/0296190 A1* 9/2022 Fukazu .................. A61B 6/469

FOREIGN PATENT DOCUMENTS

EP 3135201 B1 4/2020

* cited by examiner

*Primary Examiner* — Stephen P Coleman

(57) ABSTRACT

A medical imaging system includes an imaging apparatus including an X-ray source and a detector, wherein the X-ray source and the detector are capable of cooperating to acquire a medical image of a subject under examination, and the medical image is formed by stitching a first number of sub-medical images, the first number being greater than or equal to 2, a display apparatus used to display a graphical user interface including a parameter configuration display window, wherein the parameter configuration display window simultaneously displays an exposure parameter for each of the first number of sub-medical images, and a control apparatus used to perform exposure according to a set exposure parameter for the first number of sub-medical images, and to generate the medical image by performing stitching according to the first number of sub-medical images after the exposure.

20 Claims, 10 Drawing Sheets

MEDICAL IMAGING METHOD AND MEDICAL IMAGING SYSTEM

CROSS-REFERENCE TO RELATED APPLICATIONS

This application is based on and claims priority to Chinese Patent Application No. 202310868958.1, filed on Jul. 14, 2023, the entire contents of which is herein incorporated by reference.

TECHNICAL FIELD

Embodiments of the present application relate to the technical field of medical imaging, and relate in particular to a medical imaging method and a medical imaging system.

BACKGROUND

In a medical imaging system, emitted X-rays from an X-ray source are directed at a subject under examination and are received by a detector after penetrating the subject under examination. The detector is divided into an array of discrete elements (such as pixels). Detector elements are read to produce an output signal on the basis of the amount or intensity of radiation impacting each pixel region. The signal is processed to produce a medical image of the subject under examination, and the medical image can be displayed on a display apparatus in the medical imaging system.

SUMMARY

Embodiments of the present application provide a medical imaging method and a medical imaging system.

According to one aspect of the embodiments of the present application, a medical imaging system is provided. A medical imaging system includes an imaging apparatus including an X-ray source and a detector, wherein the X-ray source and the detector are capable of cooperating to acquire a medical image of a subject under examination, and the medical image is formed by stitching a first number of sub-medical images, the first number being greater than or equal to 2, a display apparatus used to display a graphical user interface including a parameter configuration display window, wherein the parameter configuration display window simultaneously displays an exposure parameter for each of the first number of sub-medical images, and a control apparatus used to perform exposure according to a set exposure parameter for the first number of sub-medical images, and to generate the medical image by performing stitching according to the first number of sub-medical images after the exposure.

According to one aspect of the embodiments of the present application, a medical imaging system is provided. A medical imaging system includes a display apparatus used to display a graphical user interface including a parameter configuration window, wherein the parameter configuration window simultaneously displays an exposure parameter for each sub-medical image of a first number of sub-medical images. A medical image of a subject under examination is formed by stitching the first number of sub-medical images, the first number being greater than or equal to 2.

According to one aspect of the embodiments of the present application, a medical imaging method is provided. The method includes displaying a graphical user interface including a parameter configuration display window, wherein the parameter configuration display window simultaneously displays an exposure parameter for each sub-medical image of a first number of sub-medical images, and wherein a medical image of a subject under examination is formed by stitching the first number of sub-medical images, the first number being greater than or equal to 2. The method also includes performing exposure according to the exposure parameter for each sub-medical image, and generating the medical image by performing stitching according to the first number of sub-medical images after the exposure.

With reference to the following description and drawings, specific implementations of the embodiments of the present application are disclosed in detail, and the means by which the principles of the embodiments of the present application can be employed are illustrated. It should be understood that the embodiments of the present application are not therefore limited in scope. Within the spirit and scope of the appended claims, the embodiments of the present application comprise various changes, modifications, and equivalents.

BRIEF DESCRIPTION OF THE DRAWINGS

The included drawings are used to provide further understanding of embodiments of the present application, which constitute a part of the description and are used to illustrate embodiments of the present application and explain the principles of the present application together with textual description. Evidently, the drawings in the following description are merely some embodiments of the present application, and a person of ordinary skill in the art may obtain other embodiments according to the drawings without involving inventive skill. In the drawings.

DETAILED DESCRIPTION

The foregoing and other features of the embodiments of the present application will become apparent from the following description and with reference to the drawings. In the description and drawings, specific embodiments of the present application are disclosed in detail, and part of the implementations in which the principles of the embodiments of the present application may be employed therein are indicated. It should be understood that the present application is not limited to the described implementations. On the contrary, the embodiments of the present application include all modifications, variations, and equivalents which fall within the scope of the appended claims.

In the embodiments of the present application, the terms "first" and "second" and so on are used to distinguish different elements from one another by their title, but do not represent the spatial arrangement, temporal order, or the like of the elements, and the elements should not be limited by said terms. The term "and/or" includes any one of and all combinations of one or more associated listed terms. The terms "comprise", "include", "have", etc., refer to the presence of stated features, elements, components, or assemblies, but do not exclude the presence or addition of one or more other features, elements, components, or assemblies. The terms "connect", "connected", "couple", as well as other similar terms to which the embodiments of the present application relate are not limited to physical or mechanical connections, but may include electrical connections, whether directly connected or indirectly connected.

In the embodiments of the present application, the singular forms "a", "the", and the like include plural forms, and should be broadly understood as "a type of" or "a class of" rather than limited to the meaning of "one". In addition, the term "said" should be understood as including both the singular and plural forms, unless otherwise clearly specified in the context. In addition, the phrase "according to" should be construed as "at least in part according to . . . ", and the phrase "on the basis of" should be construed as "at least in part on the basis of . . . ", unless otherwise specified in the context.

The features described and/or illustrated for one embodiment may be used in one or more other embodiments in an identical or similar manner, combined with features in other embodiments, or replace features in other embodiments. The term "include/comprise" when used herein refers to the presence of features, integrated components, steps, or assemblies, but does not exclude the presence or addition of one or more other features, integrated components, steps, or assemblies.

Figure 1:
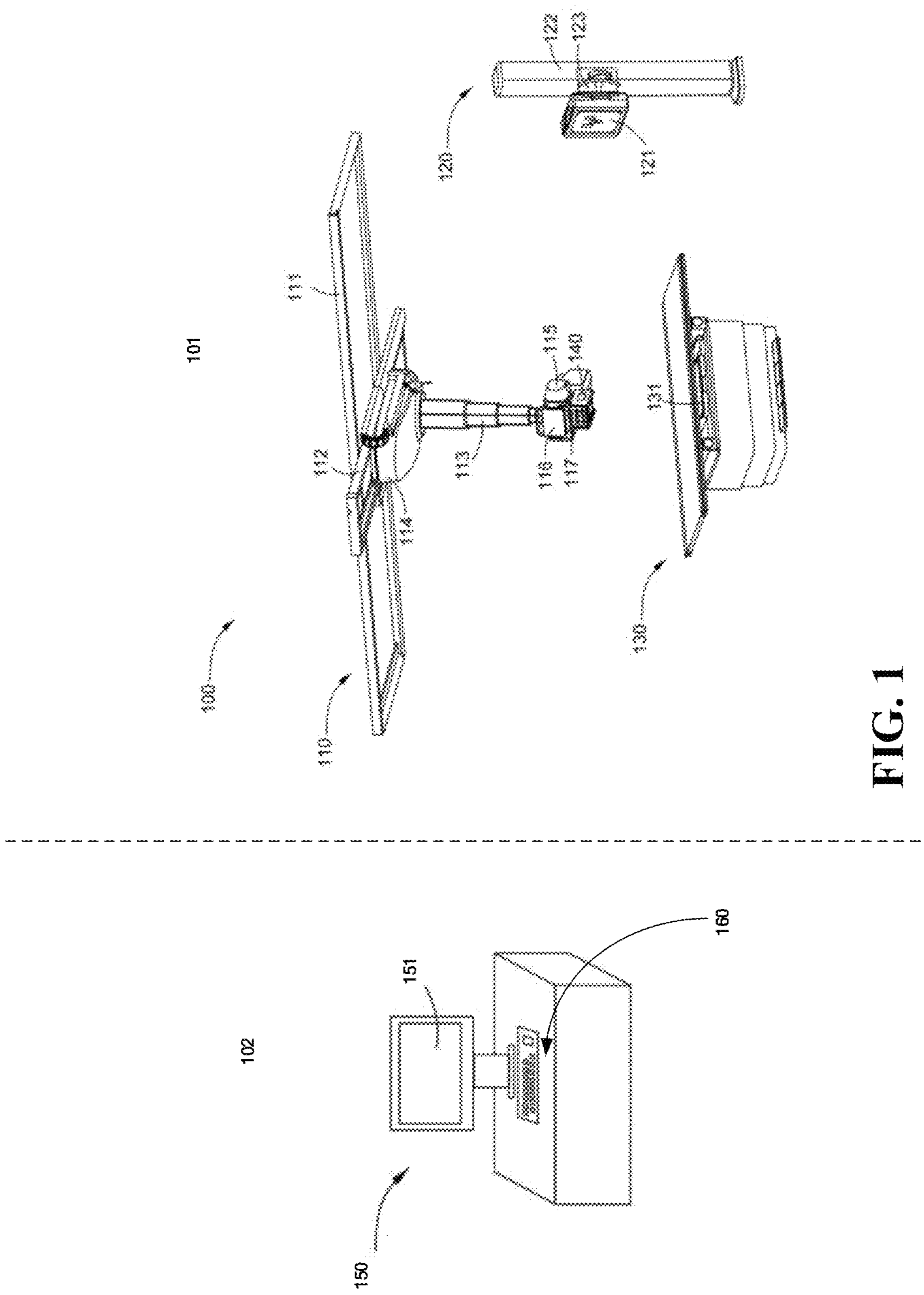
FIG. 1 is a schematic diagram of a medical imaging system of an embodiment of the present application.

FIG. 1 shows a medical imaging system 100 of an embodiment of the present application. As shown in FIG. 1, the medical imaging system 100 includes a suspension apparatus 110, a wall stand apparatus 120 and an examination table apparatus 130 provided in a scanning room 101, and a control apparatus 150 provided in a control room 102. The suspension apparatus 110 includes a longitudinal guide rail 111, a transverse guide rail 112, a telescopic cylinder 113, a sliding member 114 and a tube assembly 115.

Although some embodiments of the present application are described on the basis of a suspended X-ray imaging system, the embodiments of the present application are not limited thereto.

For ease of description, in the present application, the x-axis, y-axis, and z-axis are defined as the x-axis and the y-axis being located in a horizontal plane and being perpendicular to one another, and the z-axis being perpendicular to the horizontal plane. Specifically, the direction in which the longitudinal guide rail 111 is located is defined as the x-axis, the direction in which the transverse guide rail 112 is located is defined as the y-axis direction, and the direction of extension of the telescopic cylinder 113 is defined as the z-axis direction, and the z-axis direction is the vertical direction.

The longitudinal guide rail 111 and the transverse guide rail 112 are perpendicularly arranged, wherein the longitudinal guide rail 111 is mounted on a ceiling, and the transverse guide rail 112 is mounted on the longitudinal guide rail 111. The telescopic cylinder 113 is used to carry the tube assembly 115.

The sliding member 114 is disposed between the transverse guide rail 112 and the telescopic cylinder 113. The sliding member 114 may include components such as a rotary shaft, a motor, and a reel. The motor can drive the reel to rotate around the rotary shaft, which in turn drives the telescopic cylinder 113 to move along the z axis and/or slide relative to the transverse guide rail. The sliding member 114 can slide relative to the transverse guide rail 112, that is, the sliding member 114 can drive the telescopic cylinder 113 and/or the tube assembly 115 to move in the y-axis direction. Furthermore, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of columns having different inner diameters, and the plurality of columns may be sleeved sequentially from bottom to top in columns located thereon to thereby achieve telescoping. The telescopic cylinder 113 can be telescopic (or movable) in the vertical direction, that is, the telescopic cylinder 113 can drive the tube assembly to move along the z-axis direction. The lower end of the telescopic cylinder 113 is further provided with a rotating part, and the rotating part may drive the tube assembly 115 to rotate.

The tube assembly 115 includes an X-ray tube, and the X-ray tube may produce X-rays and project the X-rays to a patient's expected region of interest (ROI). Specifically, the X-ray tube may be positioned adjacent to a beam limiter, and the beam limiter is used to align the X-rays with the patient's expected region of interest. At least part of the X-rays may be attenuated by means of the patient and may be incident on a detector 121/131.

The suspension apparatus 110 further includes a beam limiter 117, which is usually mounted below the X-ray tube, and the X-rays emitted by the X-ray tube irradiate on the body of a subject under examination by means of an opening of the beam limiter 117. The size of the opening of the beam limiter 117 determines an irradiation range of the X-rays, namely, the size of a region of an exposure field of view (FOV). The position of the X-ray tube and beam limiter 117 in the transverse direction determines the position of the exposure FOV on the body of the subject under examination. It is well known that X-rays are harmful to the human body, so it is necessary to control the X-rays so that the X-rays irradiate only the site of the subject under examination that needs to be examined, namely, the region of interest (ROI).

The suspension apparatus 110 further includes a tube control apparatus (console) 116. The tube control apparatus 116 is mounted on the tube assembly. The tube control apparatus 116 includes user interfaces such as a display screen and a control button for performing preparation work before image capture, such as patient selection, protocol selection, positioning, etc.

The movement of the suspension apparatus 110 includes the movement of the tube assembly along the x-axis, y-axis, and z-axis, as well as the rotation of the tube assembly in a horizontal plane (the axis of rotation is parallel to or coincides with the z-axis) and in a vertical plane (the axis of rotation is parallel to the y-axis). In the described movement, a motor is usually used to drive a rotary shaft which in turn drives a corresponding component to rotate, so as to achieve a corresponding movement or rotation, and a corresponding control component is generally mounted in the sliding member 114. An X-ray imaging unit further includes a motion control unit (not shown in the figure), and the motion control unit can control the described movement of the suspension apparatus 110. Furthermore, the motion control unit can receive a control signal to control a corresponding component to move correspondingly.

The wall stand apparatus 120 includes a first detector assembly 121, a wall stand 122, and a connecting portion 123. The connecting portion 123 includes a support arm that is vertically connected in the height direction of the wall stand 122 and a rotating bracket that is mounted on the support arm, and the first detector assembly 121 is mounted on the rotating bracket. The wall stand apparatus 120 further includes a detector driving apparatus that is provided between the rotating bracket and the first detector assembly 121. Under the drive of the detector driving apparatus, the first detector assembly 121 moves along a direction that is parallel to the height direction of the wall stand 122 in a plane that is supported by the rotating bracket, and the first detector assembly 121 may be further rotated relative to the support arm to form an angle with the wall stand. The first detector assembly 121 has a plate-like structure the orientation of which can be changed, so that the incident surface of the X-rays becomes vertical or horizontal depending on the incident direction of the X-rays.

A second detector assembly 131 is included on the examination table apparatus 130, and the selection or use of the first detector assembly 121 and the second detector assembly 131 may be determined on the basis of an image capture site of a patient and/or an image capture protocol, or may be determined on the basis of the position of the subject under examination that is obtained by the capturing of a camera, so as to perform image capture and examination at a lying or standing position. FIG. 1 merely shows a schematic diagram of a wall stand and an examination table. It should be understood by those skilled in the art that a wall stand and/or examination table in any form or arrangement may be selected or just the wall stand can be mounted, and the wall stand and/or examination table do/does not limit the entire solution of the present application.

In some embodiments, the medical imaging system includes an image capture apparatus 140 (such as a camera). The subject under examination may be captured by the image capture apparatus to obtain a captured image that includes the subject under examination, for example a static optical image or a series of optical image frames in a dynamic real-time video stream, to carry out auxiliary positioning and exposure configurations and the like. The image capture apparatus may be mounted on the suspension apparatus, for example mounted on a side edge of the beam limiter 117, and the like, and the embodiments of the present application are not limited thereto. The image capture apparatus 140 includes one or more cameras, such as a digital camera or an analog camera, or a depth camera, an infrared camera or an ultraviolet camera, or a 3D camera or a 3D scanner, or a red, green and blue (RGB) sensor, an RGB depth (RGB-D) sensor or other devices that can capture color image data of a target object.

In some embodiments, the control apparatus 150 may include a source controller and a detector controller. The source controller is used to command the X-ray source to emit X-rays for image exposure. The detector controller is used to select a suitable detector from among a plurality of detectors and to coordinate the control of various detector functions, such as automatically selecting a corresponding detector according to the position or pose of the subject under examination. Alternatively, the detector controller may perform various signal processing and filtering functions, specifically, for initial adjustment of a dynamic range, interleaving of digital image data, and the like. In some embodiments, the control apparatus may provide power and timing signals for controlling the operation of the X-ray source and the detector.

In some embodiments, the control apparatus may also be configured to use a digitized signal to reconstruct one or more required images and/or determine useful diagnostic information corresponding to a patient, wherein the control apparatus may include one or more dedicated processors, graphics processing units, digital signal processors, microcomputers, microcontrollers, application-specific integrated circuits (ASICs), field-programmable gate arrays (FPGAs), or other suitable processing apparatuses.

Of course, the X-ray imaging system may also include other numbers or configurations or forms of control apparatuses. For example, the control apparatus may be local (e.g., co-located with one or more medical imaging systems 100, for example within the same facility and/or the same local network). In other implementations, the control apparatus may be remote and thus accessible via a remote connection (e.g., via the Internet or other available remote access technologies). In a specific implementation, the control apparatus may also be configured in a cloud-like means, and may be accessed and/or used in a means that is substantially similar to the means by which other cloud-based systems are accessed and used.

The system 100 also includes a storage apparatus (not shown in the figure). A processor may store the digitized signal in a memory. For example, the memory may include a hard disk drive, a floppy disk drive, a CD-read/write drive, a digital versatile disc (DVD) drive, a flash drive, and/or a solid-state memory. The memory may also be integrated together with the processor to effectively use the footprint and/or meet expected imaging requirements.

The system 100 further includes an input apparatus 160. The input apparatus 160 may include a certain form of operator interface, such as a keyboard, a mouse, a voice-activated control apparatus, a touch screen (which may also serve as a display apparatus described later), a tracking ball or any other suitable input device. An operator may input an operating signal/control signal to the control apparatus by means of the input device.

The system 100 further includes a display apparatus 151 (such as a touch screen or a display screen). The display apparatus 151 may be used to display an operation interface such as a list for the subject under examination, the positioning or exposure configuration of the subject under examination, and an image of the subject under examination.

Generally, with regard to the size of an obtained medical image, the size is generally equal to the size of the detector (the exposure field of view). If the region of interest is within the size of the detector (the exposure field of view), then the entire region of interest can be completely presented in one image. If the region of interest exceeds the size of the detector (the exposure field of view), then the entire region of interest cannot be completely presented in one image, and it is then necessary to divide the region of interest into a plurality of regions, perform exposure imaging on each region, and then stitch together multiple acquired X-ray images to obtain a complete medical image. Hereinafter, images obtained by performing X-ray imaging in each region are referred to as sub-medical images, and the complete medical image is also referred to as a combined image or a stitched image.

At present, the sub-medical images are obtained by being independently exposed. That is to say, with regard to the sub-medical images, exposure parameters thereof are set independently, and exposure is performed according to the set exposure parameters to obtain the sub-medical images. The embodiments of the present application provide a medical imaging method and a medical image system, which enable an operator to visually examine or adjust exposure parameters for all sub-medical images, and can simplify operations and improve efficiency.

The embodiments of the present application are specifically described below.

An embodiment of the present application provides a medical imaging system. The system includes: an imaging apparatus, a display apparatus, and a control apparatus. The imaging apparatus includes an X-ray source and a detector. The X-ray source and the detector are capable of cooperating to acquire a medical image of a subject under examination, and the medical image is formed by stitching a first number (N) of sub-medical images, wherein the first number is greater than or equal to 2. The display apparatus displays a graphical user interface that includes a parameter configuration display window. The control apparatus performs exposure according to a set exposure parameter for each sub-medical image, and generates the medical image by performing stitching according to the first number of sub-medical images after the exposure. The first number N may be determined according to the size of an exposure region and the size of the detector. For example, the height direction of the detector is H, the length of the exposure region is W, and the first number N is an integer greater than or equal to W/H. Alternatively, when the first number is determined, the following also needs to be considered: the distance from the detector to the region of interest, the distance from a focal point to the detector, and the size of an overlapping portion of two adjacent sub-medical images when stitching the sub-medical images. Reference may be made to the related art for details, and the embodiments of the present application are not limited thereto. For example, when the first number is 5, five sub-medical images need to be exposed to obtain a final medical image by stitching the five sub-medical images. The sequence numbers of the five sub-medical images are #1, #2, #3, #4 and #5, and the sequence numbers may also correspond to the order of exposure of the sub-medical images. That is, after the exposure parameters for the each sub-medical image are set, exposure is performed in sequence in accordance with the order of the sequence numbers of the sub-medical images. In other words, first exposure is performed on the sub-medical image the sequence number of which is #1, and after the exposure is completed, second exposure is performed on the sub-medical image the sequence number of which is #2, and so on and so forth, until the exposure of all of the sub-medical images is completed.

For implementations regarding the imaging apparatus, the display apparatus and the control apparatus, reference may be made to the foregoing embodiment corresponding to FIG. 1, the repeated portions will not be repeated, and the differences are described in detail below.

Figure 2:
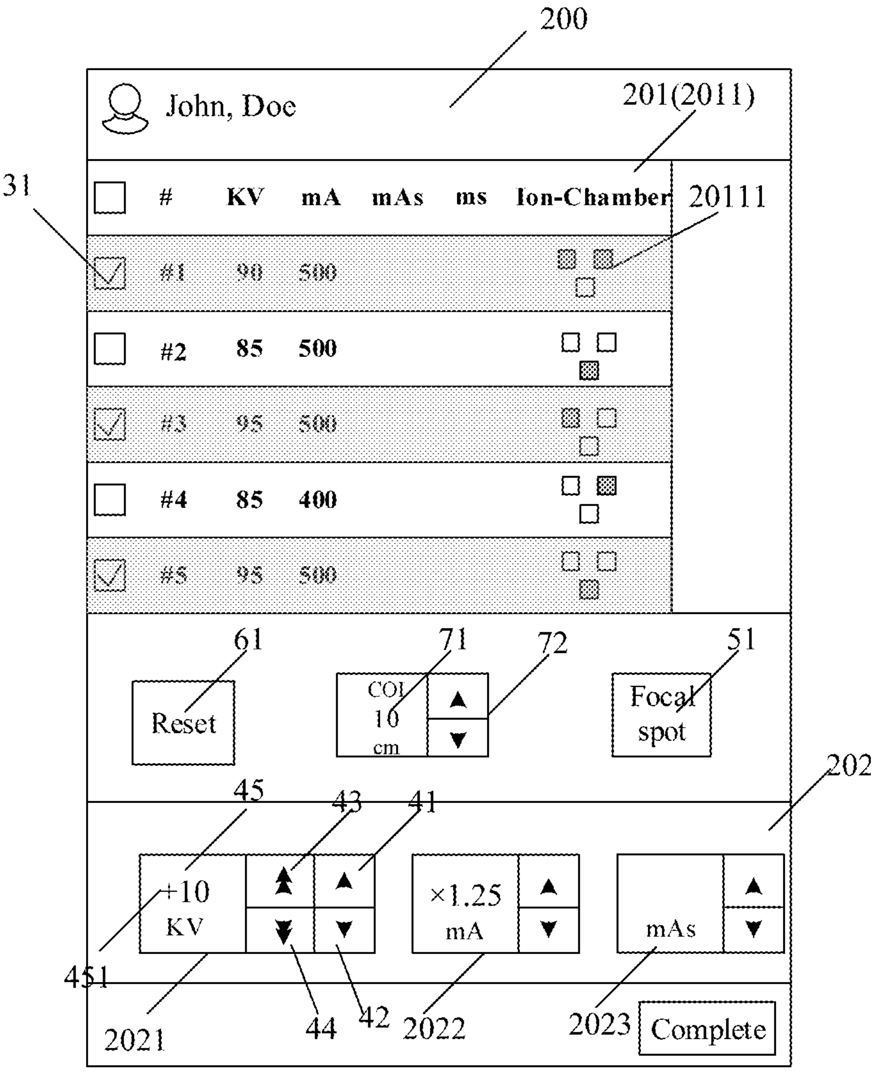
FIG. 2 is a schematic diagram of a graphical user interface of an embodiment of the present application.

FIG. 2 is a schematic diagram of a graphical user interface displayed by the display apparatus of an embodiment of the present application. As shown in FIG. 2, the graphical user interface 200 includes a parameter configuration display window 201, and the parameter configuration display window 201 simultaneously displays an exposure parameter for each sub-medical image among the first number of sub-medical images. That is to say, there is no need to switch windows or interfaces. In a window of the same interface, an operator can visually examine the exposure parameters for all of the sub-medical images, which simplifies operations, and the exposure parameters for each sub-medical image can be visually compared and displayed.

In some embodiments, the parameter configuration display window 201 includes a parameter list 2011, the parameter list 2011 including a first number of rows, different rows of the parameter list displaying exposure parameters for different sub-medical images respectively, and each row of the parameter list including a sequence number corresponding to one sub-medical image and an exposure parameter for the one sub-medical image. The exposure parameter includes at least one among a tube voltage, a tube current, a milliamp second, an exposure time, and an automatic exposure control ionization chamber. The medical imaging system may include a plurality (Z) of automatic exposure control ionization chambers (for example provided in the detector). The plurality of automatic exposure control ionization chambers may be distributed in different positions on the detector. The X-ray tube can produce X rays, and the automatic exposure control ionization chamber can detect the amount of X-rays received after passing through the subject under examination. If the amount of X-rays exceeds a predetermined amount, then the automatic exposure control ionization chamber can send a notification signal to the control apparatus, and the control apparatus can stop the irradiation of X-rays. Thus, the amount of emitted X-rays is adjusted via the automatic exposure control ionization chamber. Before exposure, an automatic exposure control ionization chamber at a position corresponding to the position of the region of interest may be selected or set to perform automatic exposure control.

In some embodiments, the list represents a corresponding exposure parameter by means of a numerical value or a character or a graphical object. For example, the tube voltage, tube current, milliamp second and exposure time may be displayed as numerical values representing the size of a corresponding exposure parameter. The automatic exposure control ionization chamber may be displayed as a character (such as L, M and R) or displayed as a graphical object (such as a rectangular box), and the character or the graphical object represents an automatic exposure control ionization chamber selected by the operator, namely, indicating which automatic exposure control ionization chamber among the Z automatic exposure control ionization chambers performs exposure control.

As shown in FIG. 2, the first number M=5, and the exposure parameters include a tube voltage (KV), a tube current (mA), a milliamp second (mAs), an exposure time (ms), and an automatic exposure control ionization chamber (Ion-Chamber). The parameter list 2011 includes five rows, and different rows of the parameter list display exposure parameters for different sub-medical images, wherein a first row of the parameter list includes a sequence number #1 of the sub-medical image the sequence number of which is #1 and exposure parameters corresponding to the sub-medical image; a second row of the parameter list includes a sequence number #2 of the sub-medical image the sequence number of which is #2 and exposure parameters corresponding to the sub-medical image; a third row of the parameter list includes a sequence number #3 of the sub-medical image the sequence number of which is #3 and exposure parameters corresponding to the sub-medical image; a fourth row of the parameter list includes a sequence number #4 of the sub-medical image the sequence number of which is #4 and exposure parameters corresponding to the sub-medical image; and a fifth row of the parameter list includes a sequence number #5 of the sub-medical image the sequence number of which is #5 and exposure parameters corresponding to the sub-medical image.

In some embodiments, initial values of exposure parameters for each sub-medical image displayed in the parameter configuration display window are default values (a numerical value is a default size, or a character or graphical object is a default character or graphical object, and a numerical value is used below as an example), the default values of the exposure parameters for the sub-medical images may be the same or different, and the embodiments of the present application are not limited thereto. The default value may be any value. For example, the default value may be the largest value or smallest value or average value of the numerical range of the exposure parameter; or the default value is related to one or more among the following: an anatomical location to be imaged, the size of the subject under examination (the size of the subject under examination may include thickness information of the subject under examination), the distance from the X-ray source to the detector, the field of view of the imaging apparatus, an automatic exposure control ionization chamber mode, a focal spot size, and the configuration of a grid.

In some embodiments, according to the above-mentioned factors related to the default values (such as the size of the subject under examination and the distance from the X-ray source to the detector), the control apparatus may perform calculation to obtain recommended exposure parameter values for the sub-medical images by using a method such as an artificial intelligence algorithm (such as a deep learning network), a standard scanning protocol library, a database or a look-up table (LUT), and use the values as default values, and the initial values of the exposure parameters for each sub-medical image displayed in the parameter configuration display window are the recommended exposure parameters. The above-mentioned recommended exposure parameter values are used as set exposure parameters. Therefore, the operator does not need to adjust the exposure parameters, and the control apparatus may perform exposure on each sub-medical image according to the above-mentioned recommended exposure parameter values. For implementations regarding the artificial intelligence algorithm, reference may be made to the related art, and the embodiments of the present application are not limited thereto.

In some embodiments, the operator may further adjust the default values of the exposure parameters initially displayed in the parameter configuration display window, and use the adjusted exposure parameter values as the set exposure parameters, and the control apparatus may perform exposure on each sub-medical image according to the adjusted exposure parameter values. An explanation for how to adjust the exposure parameter values is provided below.

In some embodiments, the system may include: an input apparatus used to receive a second input operation for adjusting exposure parameters for a second number of sub-medical images among the first number (Q) of sub-medical images; the second number is greater than or equal to 1 and less than or equal to the first number; and the control apparatus performs exposure according to the exposure parameter for each sub-medical image after the adjustment by the second input operation. That is, the operator may simultaneously adjust the exposure parameters for one or more sub-medical images.

In some embodiments, when the second number is 1, the exposure parameter corresponding to one sub-medical image is adjusted, and the exposure parameter for the one sub-medical image displayed in the parameter configuration display window is updated in real time to the adjusted exposure parameter. That is, the second input operation adjusts, only for one sub-medical image, an exposure parameter, and the exposure parameters for other sub-medical images are not adjusted. When the second input operation adjusts the exposure parameter for said sub-medical image, the parameter configuration display window simultaneously displays the adjusted exposure parameter. When the exposure parameters for a plurality of sub-medical images all need to be adjusted, the operator may adjust the exposure parameters for the sub-medical images one by one according to the second input operation. That is, the second input operation may be performed to adjust the exposure parameter for one sub-medical image, and if the exposure parameters for a plurality of sub-medical images need to be adjusted, then the second input operation is performed separately for different sub-medical images to separately adjust the exposure parameters for each sub-medical image among the plurality of sub-medical images.

In some embodiments, when the second number is greater than 1, the exposure parameters for the second number of sub-medical images are adjusted simultaneously, and the exposure parameters for the second number of sub-medical images displayed in the parameter configuration display window are updated in real time to the adjusted exposure parameters. That is, the second input operation adjusts, for the Q sub-medical images, exposure parameters therefor. When the second input operation adjusts the exposure parameters for the Q sub-medical images, the parameter configuration display window simultaneously displays the adjusted exposure parameters. That is, the second input operation may be performed to simultaneously adjust the exposure parameters for the Q sub-medical images, thereby further simplifying the operations and steps of adjusting parameters, and reducing parameter adjustment time.

In some embodiments, optionally, the input apparatus further receives a first input operation for selecting the second number of sub-medical images, first determines, by means of the first input operation, Q sub-medical images the exposure parameters for which need to be adjusted among the first number of sub-medical images, and then adjusts exposure parameters for the selected Q sub-medical images by means of the second input operation. As shown in FIG. 2, by clicking selection boxes 31, in the parameter list 2011, corresponding to rows in which the Q sub-medical images the exposure parameters for which need to be adjusted are located, or by clicking any positions in the rows, the rows in which the selected Q sub-medical images are located may be highlighted. Alternatively, it may not be necessary to first select Q sub-medical images by means of the first input operation, but the exposure parameters for the Q sub-medical images are directly adjusted by means of the second input operation, and the embodiments of the present application are not limited thereto.

In some embodiments, the graphical user interface further includes parameter adjustment markers corresponding to the exposure parameters, and when the second input operation triggers the parameter adjustment markers, the exposure parameters for the Q sub-medical images displayed in the parameter configuration display window are updated in real time to the adjusted exposure parameters. The number of parameter adjustment markers can be one or more, that is, for a plurality of exposure parameters, the same parameter adjustment marker may be used to adjust the exposure parameter values, or different parameter adjustment markers may be configured for different exposure parameters to adjust the exposure parameter values. The parameter adjustment marker may be located beside a corresponding exposure parameter in the foregoing parameter list 2011, or the graphical user interface may also include a parameter adjustment window, and the parameter adjustment marker may be located in the parameter adjustment window, and the embodiments of the present application are not limited thereto. The parameter adjustment marker includes a virtual key or other graphical objects, and the second input operation for triggering includes clicking a corresponding marker by moving a cursor. The foregoing clicking and the clicking to be described below include a touch screen click or a mouse click (long press or short press), and the like, and the embodiments of the present application are not limited thereto.

As shown in FIG. 2, the graphical user interface further includes a parameter adjustment window 202, and the parameter adjustment window 202 includes a parameter adjustment marker 2021 corresponding to an exposure parameter tube voltage, a parameter adjustment marker 2022 corresponding to an exposure parameter tube current, and a parameter adjustment marker 2023 corresponding to an exposure parameter milliamp second. The parameter adjustment marker 2021 is used below as an example to provide an explanation, and implementations of the parameter adjustment markers 2022 and 2023 are similar to that of the parameter adjustment marker 2021.

In some embodiments, the parameter adjustment marker 2021 includes a first increase marker 41 and a first decrease marker 42. When the second input operation triggers the first increase marker 41, the exposure parameters for the Q sub-medical images are simultaneously increased by a first numerical value or scaled-up by a first numerical value factor, and when the second input operation triggers the first decrease marker 42, the exposure parameters for the Q sub-medical images are simultaneously decreased by a second numerical value or scaled-down by a second numerical value factor.

In some embodiments, optionally, the parameter adjustment marker 2021 further includes a second increase marker 43 and a second decrease marker 44. When the second input operation triggers the second increase marker 43, the exposure parameters for the Q sub-medical images are simultaneously increased by a third numerical value or scaled-up by a third numerical value factor, and when the second input operation triggers the second decrease marker 44, the exposure parameters for the Q sub-medical images are simultaneously decreased by a fourth numerical value or scaled-down by a fourth numerical value factor. The third numerical value is different from the first numerical value, and the fourth numerical value is different from the second numerical value. For example, the third numerical value is less than the first numerical value, and the fourth numerical value is less than the second numerical value. Thus, the exposure parameters may be coarsely adjusted by means of the first increase marker 41 and the first decrease marker 42, and the exposure parameters may be finely adjusted by means of the second increase marker 43 and the second decrease marker 44, so that the adjustment of the exposure parameters is more flexible.

Figure 3:
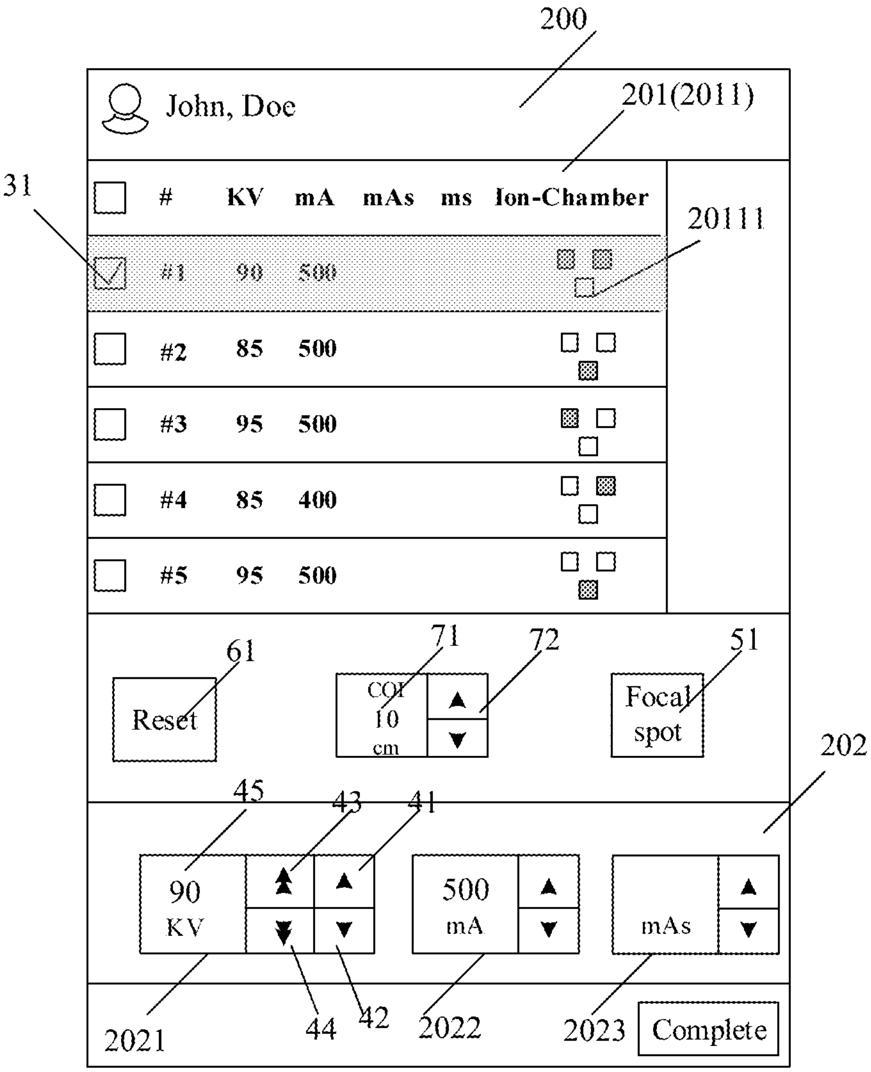
FIG. 3 is a schematic diagram of a graphical user interface of an embodiment of the present application.

In some embodiments, when Q is 1, the second input operation is used to adjust the absolute value of an exposure parameter for one sub-medical image; and when Q is greater than 1, the second input operation is used to adjust relative change values of the exposure parameters for the second number of sub-medical images. FIG. 3 is another schematic diagram of a graphical user interface of an embodiment of the present application. As shown in FIGS. 2 and 3, the graphical user interface further includes an adjustment display window 45 corresponding to the parameter adjustment marker. When Q=1 and the second input operation triggers the parameter adjustment marker, the adjustment display window 45 displays the absolute value of the adjusted exposure parameter for the one sub-medical image. For example, as shown in FIG. 3, currently, for the selected sub-medical image #1 in the parameter list, the tube voltage is 80 KV, and when the second input operation triggers the first increase marker 41, the tube voltage of the sub-medical image #1 is increased by a first numerical value (10 KV), and the adjustment display window 45 displays that the voltage is updated to 90 KV. In addition, the tube voltage of the sub-medical image #1 in the parameter list is also updated to and displayed as 90 KV. When the second input operation triggers the second increase marker 43, the tube voltage of the sub-medical image #1 is increased by a third numerical value (1 KV), the adjustment display window 45 displays that the voltage is updated to 91 KV. In addition, the tube voltage of the sub-medical image #1 in the parameter list is also updated to and displayed as 91 KV.

In some embodiments, when Q is greater than 1, and the second input operation triggers the parameter adjustment marker, the adjustment display window 45 displays relative change values of the exposure parameters for the Q sub-medical images. For example, when the second input operation triggers the first increase marker, the adjustment display window displays the first numerical value; or when the second input operation triggers the second increase marker, the adjustment display window displays the third numerical value; or when the second input operation triggers the first decrease marker, the adjustment display window displays the second numerical value; or when the second input operation triggers the second decrease marker, the adjustment display window displays the fourth numerical value. Optionally, when Q is greater than 1, the adjustment display window 45 further displays an image marker 451 representing a corresponding adjustment operation type, and the adjustment operation type includes increase (e.g., represented by using graphical object +) or decrease (e.g., represented by using graphical object −), or scale-up (e.g., represented by using graphical object ×) or scale-down (e.g., represented by using graphical object ÷). For example, as shown in FIG. 2, for the selected sub-medical images #1, #3 and #5 in the current parameter list, the tube voltages are 80 KV, 85 KV and 85 KV, respectively. When the second input operation triggers the first increase marker 41, the tube voltages of the sub-medical images #1, #3 and #5 are simultaneously increased by the first numerical value (10 KV), and the adjustment display window 45 displays +10 KV. In addition, the tube voltage of the sub-medical image #1 in the parameter list is also updated to and displayed as 90 KV, 95 KV and 95 KV. When the second input operation triggers the second increase marker 43, the tube voltages of the sub-medical images #1, #3 and #5 are simultaneously increased by the third numerical value (1 KV), and the adjustment display window 45 displays +1 KV. In addition, the tube voltages of the sub-medical images #1, #3 and #5 in the parameter list are also updated to and displayed as 91 KV, 96 KV and 96 KV.

Figure 4:
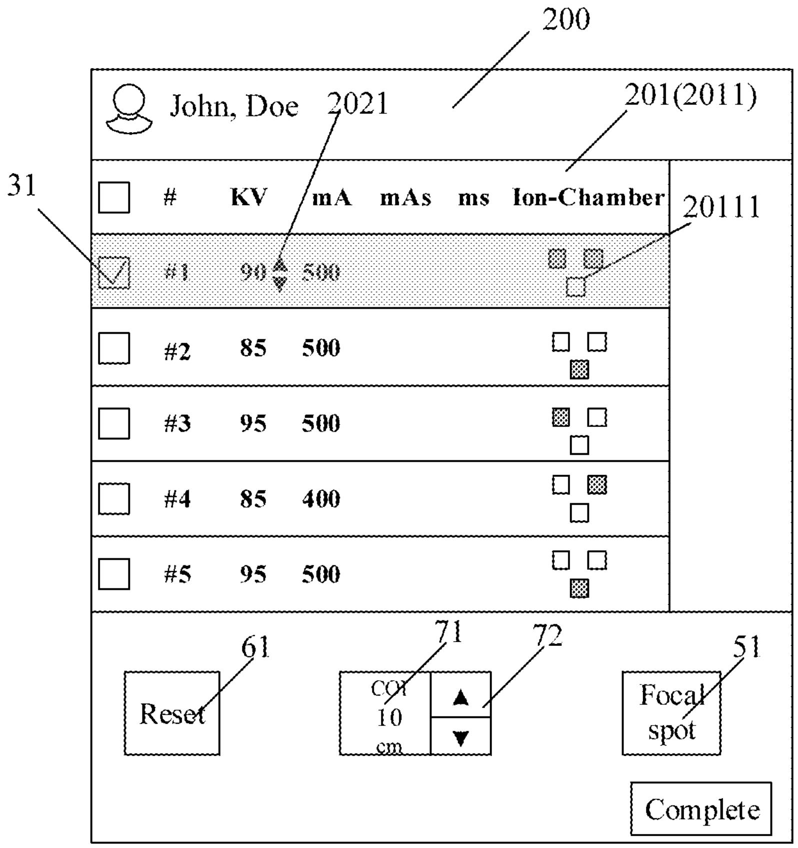
FIG. 4 is a schematic diagram of a graphical user interface of an embodiment of the present application.

In the above embodiments, a parameter adjustment marker being located in the parameter adjustment window 202 is used as an example to provide an explanation, but the embodiments of the present application are not limited thereto. FIG. 4 is another schematic diagram of a graphical user interface of an embodiment of the present application. As shown in FIG. 4, the parameter adjustment marker 2021 may also be located beside a corresponding exposure parameter in the foregoing parameter list 2011. When the second input operation triggers a corresponding parameter adjustment marker, the exposure parameter beside the parameter adjustment marker is adjusted. In said scenario, selecting Q sub-medical images by the first input operation is not necessary, and the exposure parameters may be directly adjusted by means of the second input operation. For example, when the second input operation moves a cursor to the vicinity of an exposure parameter, the parameter adjustment marker is displayed beside the exposure parameter, and when the cursor is moved away from the vicinity of the exposure parameter, the parameter adjustment marker is not displayed. Alternatively, the graphical user interface may not include a parameter adjustment marker, and the second input operation includes typing. By means of the second input operation, a value of a new exposure parameter is typed at a corresponding exposure parameter in the parameter list, so as to complete the adjustment of the exposure parameter. Examples are no longer provided for each case here.

In some embodiments, the exposure parameters for the sub-medical images are limited by upper and lower limit values. When, after the adjustment by the second input operation, there is an exposure parameter for a sub-medical image that exceeds the upper limit value or that is less than the lower limit value, the exposure parameter for the sub-medical image displayed in the parameter configuration display window is updated to the upper limit value or the lower limit value. That is, when, after the adjustment by the second input operation, there is an exposure parameter for a sub-medical image that exceeds the upper limit value or that is less than the lower limit value, the exposure parameter adjustment corresponding to the second input operation will be ignored, and the control apparatus and the parameter configuration display window no longer change the exposure parameter in response to the second input operation. The control apparatus presets the upper and lower limit values of the exposure parameters for each sub-medical image. The control apparatus compares the relationship between the adjusted exposure parameter and the upper limit value. When the adjusted exposure parameter value is greater than the upper limit value, the exposure parameters for the sub-medical images displayed in the parameter configuration display window are updated to the upper limit value. Alternatively, the control apparatus compares the relationship between the adjusted exposure parameter with the lower limit value, and when the adjusted exposure parameter value is less than the lower limit value, the exposure parameters for the sub-medical images displayed in the parameter configuration display window are updated to the lower limit value. For example, for the exposure parameter tube voltage, the upper limit value thereof is preset to 200 KV and the lower limit value thereof is preset to 20 KV. The sub-medical images #1 and #3 are selected to simultaneously adjust the exposure parameters thereof. Currently, the tube voltage of the sub-medical image #1 is 195 KV, and the tube voltage of the sub-medical image #3 is 185 KV. When the second input operation is to adjust the tube voltage to increase by 10 KV, the adjusted tube voltage of the sub-medical image #1 should be 205 KV, which is greater than the upper limit value of 200 KV. Therefore, the exposure parameter for the sub-medical image displayed in the parameter configuration display window is not updated to 205 KV, but is updated to 200 KV. The adjusted tube voltage of the sub-medical image #3 should be 195 KV, which is less than the upper limit value of 200 KV. Therefore, the exposure parameter for the sub-medical image displayed in the parameter configuration display window is updated to 195 KV.

In some embodiments, the upper and lower limit values of the exposure parameter may be set as needed. Optionally, the upper and lower limit values of the exposure parameter may be related to a set focal spot size. The X-ray focal spot size of the medical imaging system may include a microfocal spot, a small focal spot, a regular focal spot, a large focal spot, etc. For example, a small focal spot is typically defined to be between 0.1 mm and 0.6 mm, and a large focal spot is between 0.6 mm and 1.8 mm. For focal spots of different sizes, different upper and lower limit values may be set. For example, for the exposure parameter tube voltage, the set upper limit value is 300 KV for the small focal spot and is 400 KV for the large focal spot. Examples are no longer provided for each case here.

In some embodiments, as shown in FIGS. 2 and 3, the graphical user interface further includes a focal spot adjustment marker 51 (a virtual key or another graphical object). When the input apparatus receives a fourth input operation for triggering the focal spot adjustment marker, the size of the focal spot may be switched. For example, the fourth input operation for triggering includes clicking a corresponding marker by moving a cursor. When the current focal spot is a small focal spot, the spot may be switched to a large focal spot upon receiving the fourth input operation; and when the current focal spot is a large focal spot, the spot may be switched to a small focal spot upon receiving the fourth input operation. The embodiments of the present application are not limited thereto. For example, when the current focal spot is a small focal spot, the spot may be switched to a regular focal spot upon receiving the fourth input operation, switched to a large focal spot upon again receiving the fourth input operation, and switched to a small focal spot upon again receiving the fourth input operation, and so on. Examples are no longer provided for each case here. In addition, in the focal spot adjustment marker 51, graphical object styles of markers corresponding to different focal spot sizes may be different.

In some embodiments, the upper or lower limit value of the foregoing exposure parameter is an upper or lower limit value corresponding to an adjusted focal spot; and when there is an exposure parameter for a sub-medical image in the parameter configuration display window that exceeds the adjusted upper limit value or that is less than the adjusted lower limit value, the exposure parameter for the sub-medical image displayed in the parameter configuration display window is updated to the adjusted upper limit value or the adjusted lower limit value. For example, for the exposure parameter tube voltage, the upper limit value corresponding to the small focal spot is preset to 200 KV and the upper limit value corresponding to the large focal spot to 300 KV. When the currently set tube voltage is 295 KV and the large focal spot is currently set, and when the second input operation is to adjust the tube voltage to increase by 10 KV, the adjusted tube voltage should be 305 KV, which is greater than the upper limit value of 300 KV. Therefore, the tube voltage of the sub-medical image displayed in the parameter configuration display window is not updated to 305 KV, but is updated to 300 KV. However, if the fourth input operation is received at this time, and when switched to the small focal spot, the tube voltage for the sub-medical image displayed in the parameter configuration display window is updated to 200 KV. The above is an example of adjusting the exposure parameter for one sub-medical image, and is similar to implementations when simultaneously adjusting the exposure parameters for a plurality of sub-medical images; therefore, details will not be repeated here.

In some embodiments, as shown in FIGS. 2 and 3, the graphical user interface further includes an exposure parameter reset marker 61 (a virtual key or another graphical object). When the input apparatus receives a third input operation for triggering the exposure parameter reset marker, the exposure parameters for the first number of sub-medical images displayed in the parameter configuration display window are all updated to default values; or the exposure parameters for the second number of sub-medical images displayed in the parameter configuration display window are updated to default values. When the second number is 1 and the third input operation triggers the exposure parameter reset marker, an exposure parameter corresponding to one sub-medical image is reset, and the exposure parameter for the one sub-medical image displayed in the parameter configuration display window is updated to a default value; or when the second number is greater than 1 and the third input operation triggers the exposure parameter reset marker, the exposure parameters for the second number of sub-medical images are reset simultaneously, and the exposure parameters for the second number of sub-medical images displayed in the parameter configuration display window are updated to default values. For example, the third input operation for triggering includes clicking a corresponding marker by moving a cursor, and when the third input operation is received, the exposure parameters for all of the sub-medical images are restored to default values; or when Q=1, only the exposure parameter for one selected sub-medical image is restored to a default value; or when Q is greater than 1, the exposure parameters for Q selected sub-medical images are restored to default values. Thus, when the operator incorrectly adjusts the exposure parameter, initial configurations can be quickly restored.

In the above example, an exposure parameter being the tube voltage is used as an example to provide an explanation. For other exposure parameters, such as the tube current, the milliamp second, and the exposure time, the adjustment means are similar, and examples are no longer provided for each case here. For the exposure time, since the milliamp second is equal to tube current×exposure time+1000, the exposure time may also be adjusted by adjusting the milliamp second after configuring the tube current, and the embodiments of the present application are not limited thereto.

In some embodiments, the medical imaging system may further include an image capture apparatus, which captures the subject under examination to obtain a captured image including the subject under examination. In addition, the captured image obtained by the image capture apparatus capturing the subject under examination may be displayed on the display apparatus. The captured image is distinguished from a medical image obtained by performing X-ray imaging, and is used for an auxiliary positioning or exposure configuration. For example, the auxiliary positioning or exposure configuration includes obtaining information of the subject under examination, obtaining the capturing protocol, and determining a radiation dose, posture and other information, performing positioning on the basis of the capturing protocol, and configuring the size and position of an exposure region, and the like.

Figure 5:
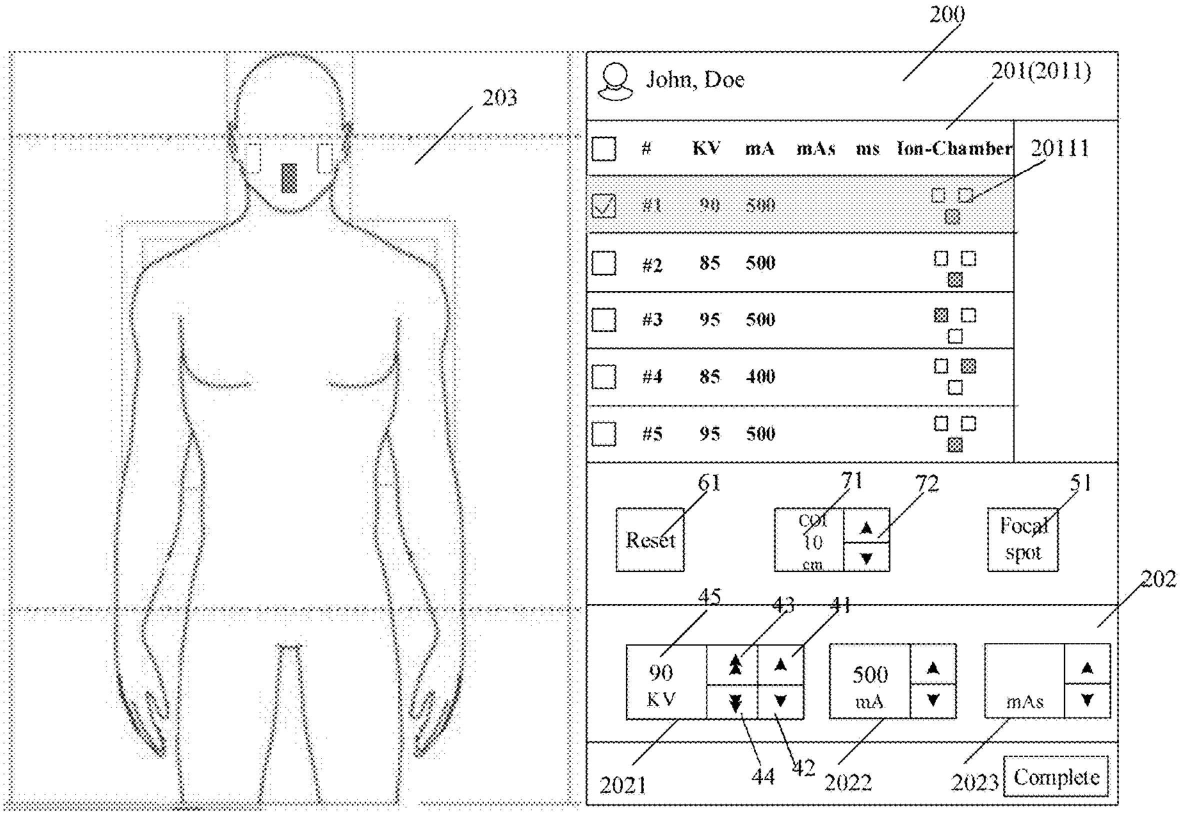
FIG. 5 is a schematic diagram of a graphical user interface of an embodiment of the present application.

FIG. 5 is another schematic diagram of a graphical user interface of an embodiment of the present application. As shown in FIG. 5, the graphical user interface may further include a region 203 that displays the captured image. After selecting Q sub-medical images, markers for switch states of a plurality (Z) of automatic exposure control ionization chambers corresponding to the Q sub-medical images are superimposed and displayed at positions corresponding to the sub-medical images in the captured image. The states of the automatic exposure control ionization chambers corresponding to the Q sub-medical images are set as ON or OFF by triggering the markers for the switch states; and the states of automatic exposure control ionization chambers corresponding to each sub-medical image are simultaneously displayed in the parameter configuration display window. For each sub-medical image, the markers for the Z automatic exposure control ionization chambers are superimposed and displayed respectively, and the superimposed and displayed positions do not represent the real positions thereof, but only represent the relative positions of the Z automatic exposure control ionization chambers. One rectangular box may be used as a marker for one automatic exposure control ionization chamber, or different graphical objects may also be used as markers for different automatic exposure control ionization chambers, and the embodiments of the present application are not limited thereto.

Figure 6:
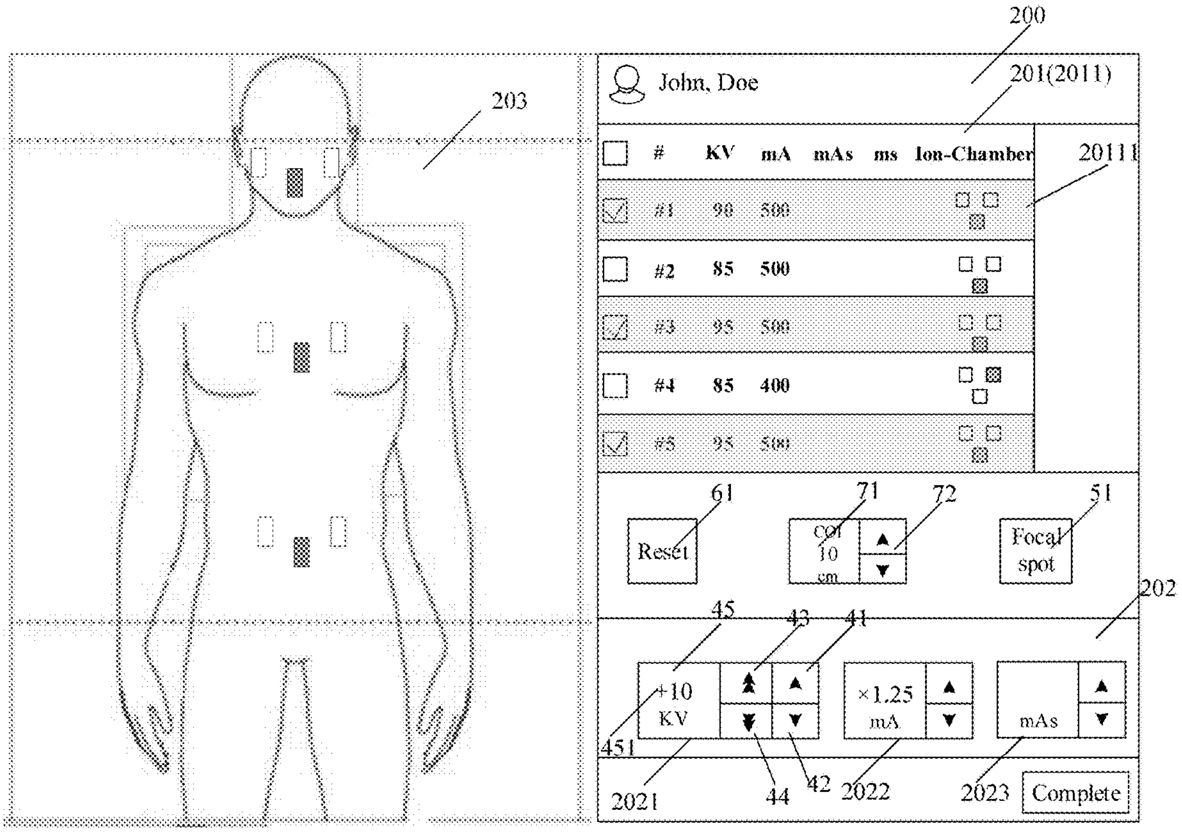
FIG. 6 is a schematic diagram of a graphical user interface of an embodiment of the present application.
Figure 7:
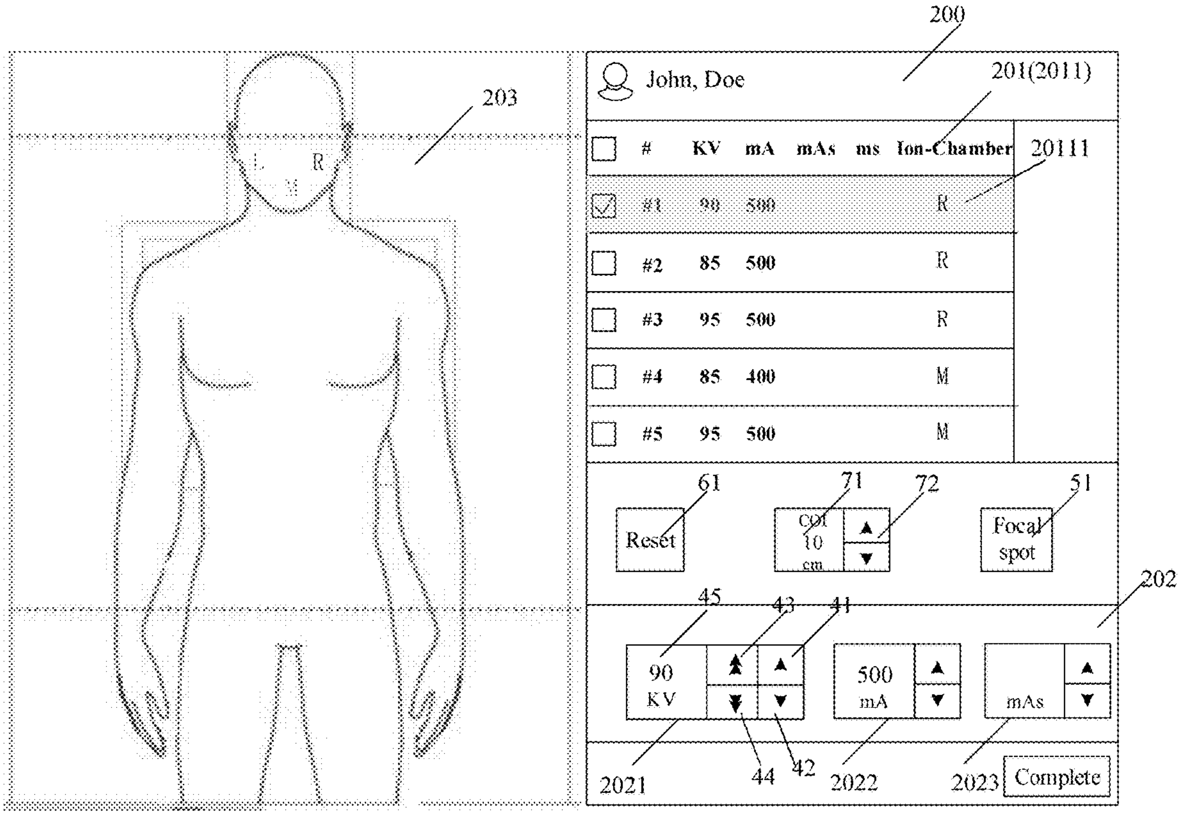
FIG. 7 is a schematic diagram of a graphical user interface of an embodiment of the present application.
Figure 8:
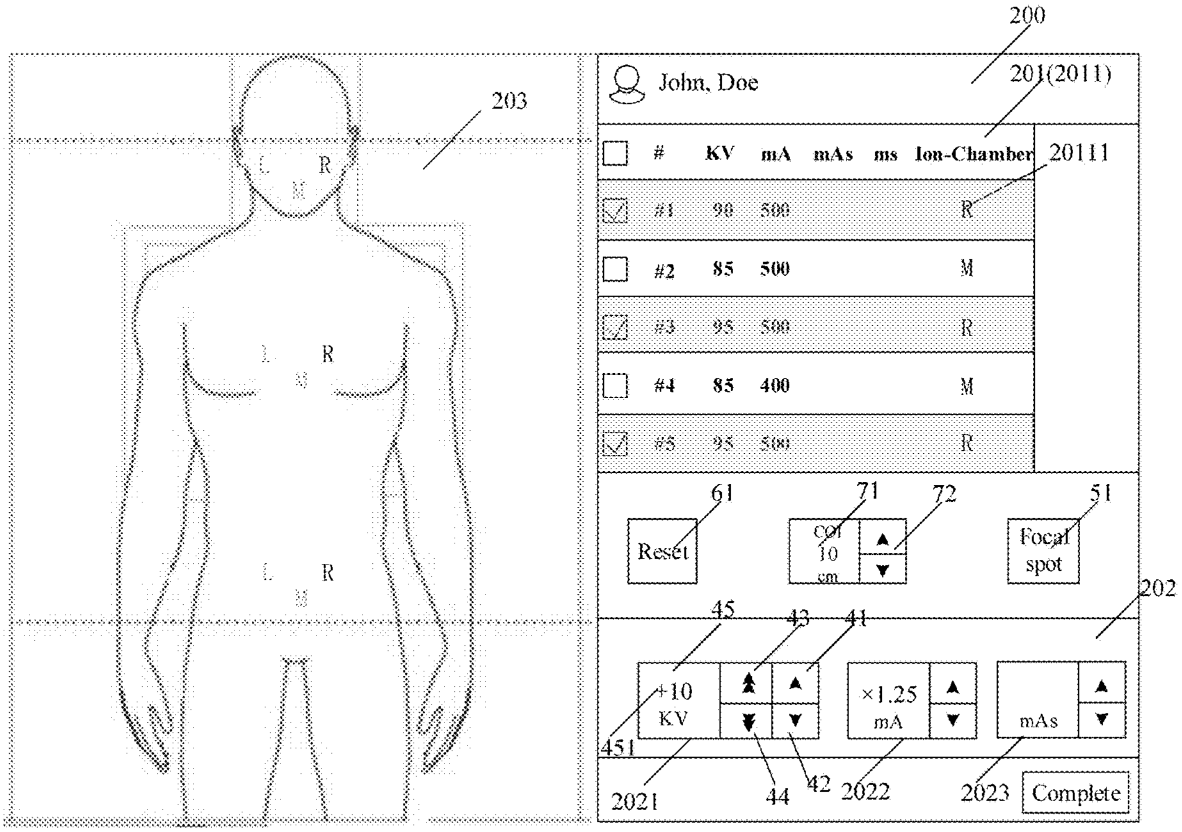
FIG. 8 is a schematic diagram of a graphical user interface of an embodiment of the present application.

As shown in FIG. 5, taking Z=3 as an example, three automatic exposure control ionization chambers are represented by using three rectangular boxes, which are separately schematically superimposed and displayed on the captured image. As shown in FIG. 5, Q=1; therefore, three markers (three rectangular boxes) for three automatic exposure control ionization chambers are superimposed and displayed at the position corresponding to a first sub-medical image in the captured image. FIG. 6 is another schematic diagram of a graphical user interface of an embodiment of the present application, and Q=3; therefore, three markers (three rectangular boxes) for three automatic exposure control ionization chambers are separately superimposed and displayed at the position corresponding to each sub-medical image in the captured image. FIGS. 7 and 8 are schematic diagrams of a graphical user interface of an embodiment of the present application, and differ from FIGS. 5 and 6 in that the markers for automatic exposure control ionization chambers are represented by using different letters. Taking M=3 as an example, the markers for three automatic exposure control ionization chambers are represented by using R, M and L, respectively.

In some embodiments, the display apparatus further needs to superimpose and display, on the captured image, the switch states of Z automatic exposure control ionization chambers corresponding to the selected one or more sub-medical images, wherein an ON state or an OFF state may be distinguished by the style change of the foregoing markers for the automatic exposure control ionization chambers. The switch state does not represent the current switch state of the automatic exposure control ionization chamber, but the switch state of the automatic exposure control ionization chamber after the exposure operation starts. The ON state represents that the corresponding automatic exposure control ionization chamber is selected and used for automatic exposure control after the exposure operation starts, and the OFF state represents that the corresponding automatic exposure control ion chamber is not selected and is not used for automatic exposure control after the exposure operation starts. As shown in FIGS. 5 and 6, the ON state or OFF state may be distinguished by using rectangles of different fill colors. For example, a white rectangle is used to represent the OFF state (not selected), a dark rectangle is used to represent the ON state (selected), or vice versa. The embodiments of the present application are not limited thereto. The ON state or OFF state may also be distinguished by using rectangles of different sizes. For example, a small rectangle can be used to represent the OFF state (not selected), and a large rectangle can be used to represent the ON state (selected). As shown in FIGS. 7 and 8, the ON state or OFF state may be distinguished by using letters of different colors. For example, gray letters can be used to represent the OFF state (not selected) and black letters can be used to represent the ON state (selected), and the like, and examples are no longer provided for each case here.

In some embodiments, when the markers for the plurality of automatic exposure control ionization chambers are initially superimposed and displayed, the markers may all be in the OFF state by default, or one thereamong may be in the ON state by default and others in the OFF state by default, and the embodiments of the present application are not limited thereto.

In some embodiments, the input apparatus may receive an input operation (a fifth input operation) for configuring the switch states of the plurality of automatic exposure control ionization chambers. The fifth input operation includes triggering (by moving a cursor to click or touch) a marker for one automatic exposure control ionization chamber among the markers for the superimposed and displayed Z automatic exposure control ionization chambers. After the input operation is received, the control apparatus selects, according to the received input operation for configuring the switch states of the plurality of automatic exposure control ionization chambers, an automatic exposure control ionization chamber in an ON state to perform exposure time control. For example, after the fifth input operation is received, the style of the triggered marker for the automatic exposure control ionization chamber changes, which represents that the switch state is switched. For example, when the marker for the automatic exposure control ionization chamber is a white rectangle, after the marker is triggered, the marker is changed to a dark rectangle, which represents that the automatic exposure control ionization chamber at the position corresponding to the marker is selected, and the automatic exposure control ionization chamber is in the ON state for automatic exposure control after the exposure operation starts.

In some embodiments, when only one automatic exposure control ionization chamber in the ON state may be selected for one sub-medical image, upon receiving the fifth input operation, the automatic exposure control ionization chamber corresponding to the triggered marker for the automatic exposure control ionization chamber is changed to the ON state (for example, changing from a white rectangle to a dark rectangle), and when an automatic exposure control ionization chamber corresponding to a non-triggered marker for the automatic exposure control ionization chamber is in the ON state (for example, there is a dark rectangle that has not been triggered), synchronously with the fifth input operation, the control apparatus changes the automatic exposure control ionization chamber corresponding to the non-triggered marker for the automatic exposure control ionization chamber to the OFF state, that is, the display apparatus synchronously updates and displays the style of the non-triggered marker for the automatic exposure control ionization chamber (for example, changing from a dark rectangle to a white rectangle).

In some embodiments, as shown in FIGS. 5 to 8, the parameter configuration display window 201 may also simultaneously display the switch states 20111 of a plurality of automatic exposure control ionization chambers corresponding to sub-medical images. The switch states of the plurality of automatic exposure control ionization chambers displayed corresponding to the sub-medical images in the parameter configuration display window are the same as the switch states of the plurality of automatic exposure control ionization chambers superimposed and displayed at the corresponding sub-medical image positions of the captured image.

In some embodiments, as shown in FIGS. 2 and 3, the graphical user interface further includes a distance information display window 71 for filling in or adjusting or displaying the distance between the center of a region of interest and a detector plane, wherein when medical imaging of the subject under examination is performed, the subject under examination is standing on a stitching frame. The stitching frame refers to a support frame placed in front of the detector. The stitching frame is provided with a scale. The metric value of the scale is read by the operator, so that the distance between the center of the region of interest and the stitching frame can be directly determined. Since the distance between the stitching frame and the detector plane is fixed, the distance between the center of the region of interest and the detector plane can be determined, and the operator can fill in and display the read metric value of the scale in the distance information display window 71. In addition, the distance information display window 71 further includes an adjustment button 72 for adjusting the size of the distance. For implementations of the adjustment button 72, reference may be made to the first increase marker and the first decrease marker, and details will not be repeated here.

Figure 9:
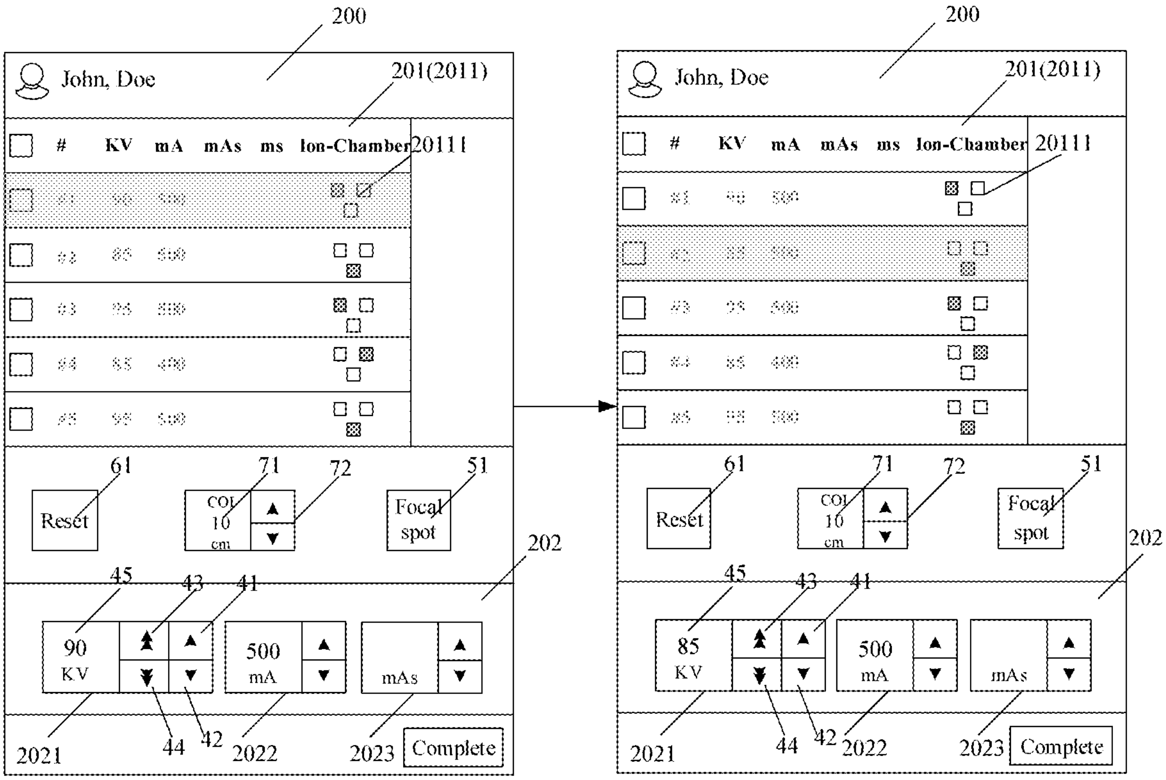
FIG. 9 is a schematic diagram of a graphical user interface of an embodiment of the present application.

In some embodiments, the control apparatus performs exposure according to the set exposure parameter for each sub-medical image, wherein when the control apparatus performs exposure on one sub-medical image among the first number of sub-medical images, the exposure parameter for the one sub-medical image displayed in the parameter configuration display window 201 is an exposure parameter used in a current exposure, and the exposure parameter for the one sub-medical image has a different display means from the exposure parameters for other sub-medical images. For example, FIG. 9 is another schematic diagram of a graphical user interface of an embodiment of the present application. As shown in FIG. 9, for set exposure parameters (e.g., a configuration completion marker being triggered or a marker such as a start exposure marker being triggered represents that exposure parameters can no longer be adjusted, i.e., set exposure parameters), the exposure parameters displayed in the parameter configuration display window are locked and cannot be adjusted (e.g., they may be displayed as being in a non-editable state). When exposure is performed on the sub-medical image #1, the exposure parameters for the sub-medical image #1 in the parameter list are highlighted, the exposure parameters for the other sub-medical images are not highlighted, and the exposure parameters in a row in which the sub-medical image #1 is located in the parameter list are displayed as exposure parameters used in the current exposure. After the exposure of the sub-medical image #1 is completed, exposure is performed on the sub-medical image #2, the exposure parameters for the sub-medical image #2 in the parameter list are highlighted, the exposure parameters for the other sub-medical images are not highlighted (the exposure parameters for the sub-medical image #1 the exposure of which has been completed may be displayed as gray), and so on and so forth, until the exposure of all of the sub-medical images is completed.

In some embodiments, optionally, when exposure is performed on one sub-medical image among the first number of sub-medical images, it is also possible to display exposure parameters used in the current exposure of the one sub-medical image in the adjustment display window 45. For example, as shown in FIG. 9, when exposure is performed on the sub-medical image #1, exposure parameters (a tube voltage of 90 KV, and a tube current of 500 mA) used in the exposure of the sub-medical image #1 are displayed in the adjustment display window 45. After the exposure of the sub-medical image #1 is completed, exposure is performed on the sub-medical image #2, exposure parameters (a tube voltage of 85 KV, and a tube current of 500 mA) used in the exposure of the sub-medical image #2 are displayed in the adjustment display window 45, and so on and so forth, until the exposure of all of the sub-medical images is completed.

The above input operations may also be performed by means of voice, and the embodiments of the present application are not limited thereto.

The above embodiments merely provide illustrative descriptions of the embodiments of the present application. However, the present application is not limited thereto, and appropriate variations may be made on the basis of the above embodiments. For example, each of the above embodiments may be used independently, or one or more of the above embodiments may be combined.

Figure 10:
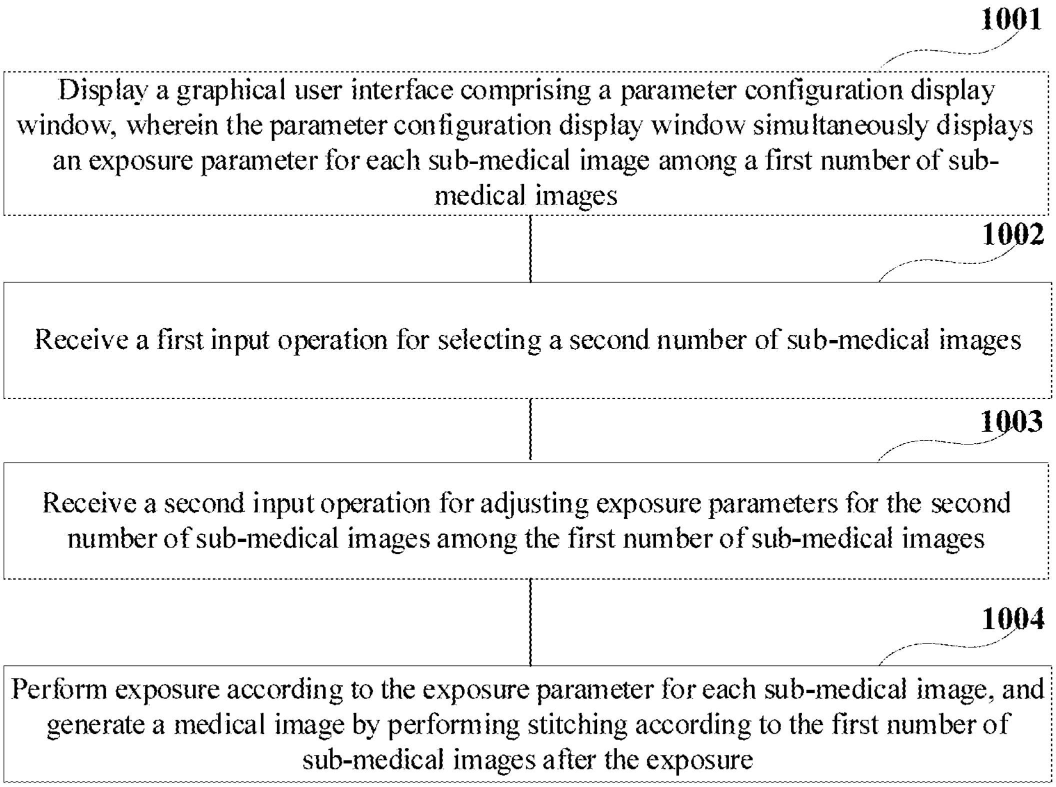
FIG. 10 is a schematic diagram of a medical imaging method of an embodiment of the present application.

An embodiment of the present application further provides a medical imaging method, and the same content as that of the embodiments of the foregoing aspects is not repeated. FIG. 10 is a schematic diagram of a medical imaging method of an embodiment of the present application. As shown in FIG. 10, the method includes:

1001, displaying a graphical user interface including a parameter configuration display window, wherein the parameter configuration display window simultaneously displays an exposure parameter for each sub-medical image of a first number of sub-medical images, and wherein a medical image of a subject under examination is formed by stitching the first number of sub-medical images, the first number being greater than or equal to 2; and

1004, performing exposure according to the exposure parameter for each sub-medical image, and generating the medical image by performing stitching according to the first number of sub-medical images after the exposure.

In some embodiments, the method may further include:

1003, receiving a second input operation for adjusting exposure parameters for a second number of sub-medical images among the first number of sub-medical images, the second number being greater than or equal to 1 and less than or equal to the first number;

and 1004, performing exposure according to the exposure parameter for each sub-medical image after the adjustment by the second input operation.

In some embodiments, the method may further include:

1002, receiving a first input operation for selecting the second number of sub-medical images.

It should be noted that FIG. 10 merely schematically illustrates the embodiment of the present application, but the present application is not limited thereto. For example, the order of execution between the operations may be suitably adjusted. In addition, some other operations may also be added or certain operations thereamong may be omitted. For example, 1002 is omitted, or 1002 and 1003 are omitted, or the like. Alternatively, at least one among the following operations may be added: when an input apparatus receives a third input operation for triggering an exposure parameter reset marker, the exposure parameters for the first number of sub-medical images displayed in the parameter configuration display window are all updated to default values; or the exposure parameters for the second number of sub-medical images displayed in the parameter configuration display window are updated to default values; and when the input apparatus receives a fourth input operation for triggering a focal spot adjustment marker, a focal spot size is switched, and the upper limit value or the lower limit value of the exposure parameter is adjusted to an upper limit value or lower limit value corresponding to an adjusted focal spot. Those skilled in the art could make appropriate variations according to the above content, rather than being limited by the above disclosure of FIG. 10.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

An embodiment of the present application further provides a graphical user interface including a parameter configuration window, wherein the parameter configuration window simultaneously displays an exposure parameter for each sub-medical image of the first number of sub-medical images, and wherein a medical image of the subject under examination is formed by stitching the first number of sub-medical images, the first number being greater than or equal to 2.

In some embodiments, the graphical user interface further includes an exposure parameter reset marker, and when the exposure parameter reset marker is triggered, the exposure parameters for the first number of sub-medical images displayed in the parameter configuration display window are all updated to default values; or the exposure parameters for the second number of sub-medical images displayed in the parameter configuration display window are updated to default values, the second number being greater than or equal to 1 and less than or equal to the first number.

In some embodiments, the graphical user interface further includes a focal spot adjustment marker, and when the focal spot adjustment marker is triggered, the upper limit value or the lower limit value of the exposure parameter is adjusted to an upper limit value or a lower limit value corresponding to an adjusted focal spot; and when there is an exposure parameter for a sub-medical image that exceeds the adjusted upper limit value or that is less than the adjusted lower limit value in the parameter configuration display window, the exposure parameter for the sub-medical image displayed in the parameter configuration display window is updated to the adjusted upper limit value or the adjusted lower limit value.

In some embodiments, the graphical user interface further comprises a region displaying a captured image and markers for switch states of a plurality of automatic exposure control ionization chambers corresponding to a second number of sub-medical images superimposed and displayed on the captured image, and the states of the automatic exposure control ionization chambers corresponding to the second number of sub-medical images are set as ON or OFF by triggering the markers for the switch states, the second number being greater than or equal to 1 and less than or equal to the first number; and the states of the automatic exposure control ionization chambers corresponding to each sub-medical image are simultaneously displayed in the parameter configuration display window.

In some embodiments, the graphical user interface further includes a distance information display window for filling in or adjusting or displaying the distance between the center of a region of interest and a detector plane.

For implementations of the windows or markers above, reference may be made to the foregoing embodiments (as shown in any one among FIGS. 2 to 9), and details will not be repeated here.

According to the medical imaging system, the medical imaging method, and the graphical user interface provided in the present application, the parameter configuration display window is designed to simultaneously display the exposure parameters for each sub-medical image among all of the sub-medical images. Thus, switching windows or interfaces is not needed. In a window of the same interface, the operator can visually examine the exposure parameters for all of the sub-medical images, which simplifies operations, and the exposure parameters for the sub-medical images can be visually compared and displayed.

In addition, the control apparatus may generate recommended exposure parameter values according to an algorithm and perform exposure according to the recommended exposure parameter values. Therefore, the operator does not need to perform exposure parameter adjustment, thereby improving efficiency. Performing exposure according to recommended parameters may also ensure exposure image quality.

In addition, performing the second input operation may support simultaneous adjustment of exposure parameters of a plurality of sub-medical images. Thus, there is no need to adjust the exposure parameters for the sub-medical images one by one, thereby further simplifying the operations and steps of adjusting parameters, and reducing parameter adjustment time.

In addition, when one sub-medical image thereamong is selected for exposure parameter adjustment, the absolute value of the exposure parameter may be directly adjusted, and when a plurality of sub-medical images are selected for exposure parameter adjustment, relative values of the plurality of sub-medical images may be simultaneously increased or decreased. Thus, there is no need to adjust the exposure parameters for the sub-medical images, thereby further simplifying the operations and steps of adjusting parameters, and reducing parameter adjustment time.

In addition, after the exposure process is performed or after the exposure is completed, the actual exposure parameters used may be displayed in the parameter configuration display window for the operator's reference.

In addition, by configuring multiple sets of parameter adjustment markers, the exposure parameters may be separately coarsely and finely adjusted, so that the adjustment of the exposure parameters is more flexible.

In addition, the adjustment of the focal spot is considered while adjusting the exposure parameters, so that the adjustment of the exposure parameters is more flexible.

In addition, by designing the exposure parameter reset marker, the initial configuration may be quickly restored when the operator incorrectly adjusts the exposure parameters.

In addition, the markers for switch states of the plurality of automatic exposure control ionization chambers are superimposed and displayed on the captured image, and the states of the automatic exposure control ionization chambers corresponding to the second number of sub-medical images are set as ON or OFF by triggering the markers for the switch states, thereby allowing the selection of automatic exposure control ionization chambers to be more visual and convenient.

The above apparatus and method of the present application can be implemented by hardware, or can be implemented by hardware in combination with software. The present application relates to the foregoing type of computer-readable program. When executed by a logic component, the program causes the logic component to implement the foregoing apparatus or a constituent component, or causes the logic component to implement various methods or steps as described above. The present application further relates to a storage medium for storing the above program, such as a hard disk, a magnetic disk, an optical disk, a DVD, a flash memory, etc.

The method/apparatus described with reference to the embodiments of the present application may be directly embodied as hardware, a software module executed by a processor, or a combination of the two. For example, one or more of the functional block diagrams and/or one or more combinations of the functional block diagrams as shown in the drawings may correspond to either software modules or hardware modules of a computer program flow. The foregoing software modules may respectively correspond to the steps shown in the figures. The foregoing hardware modules may be implemented, for example, by firming the foregoing software modules by using a field-programmable gate array (FPGA).

The software modules may be located in a RAM memory, a flash memory, a ROM memory, an EPROM memory, an EEPROM memory, a register, a hard disk, a removable disk, a CD-ROM, or any storage medium in other forms known in the art. The storage medium may be coupled to a processor, so that the processor can read information from the storage medium and can write information into the storage medium. Alternatively, the storage medium may be a component of the processor. The processor and the storage medium may be located in an ASIC. The software module may be stored in a memory of a mobile terminal, and may also be stored in a memory card that can be inserted into a mobile terminal. For example, if a device (such as a mobile terminal) uses a large-capacity MEGA-SIM card or a large-capacity flash memory apparatus, then the software modules may be stored in the MEGA-SIM card or the large-capacity flash memory apparatus.

One or more of the functional blocks and/or one or more combinations of the functional blocks shown in the drawings may be implemented as a general-purpose processor, a digital signal processor (DSP), an application-specific integrated circuit (ASIC), a field-programmable gate array (FPGA) or other programmable logic devices, a discrete gate or transistor logic device, a discrete hardware assembly, or any appropriate combination thereof, which is used for implementing the functions described in the present application. The one or more functional blocks and/or the one or more combinations of the functional blocks shown in the drawings may also be implemented as a combination of computing equipment, such as a combination of a DSP and a microprocessor, a plurality of microprocessors, one or more microprocessors in communication combination with a DSP, or any other such configuration.

The present application is described above with reference to specific embodiments. However, it should be clear to those skilled in the art that the foregoing description is merely illustrative and is not intended to limit the scope of protection of the present application. Various variations and modifications may be made by those skilled in the art according to the principle of the present application, and said variations and modifications also fall within the scope of the present application.

What is claimed is:

1. A medical imaging system comprising:

an imaging apparatus including an X-ray source and a detector, wherein the X-ray source and the detector are capable of cooperating to acquire a medical image of a subject under examination, and the medical image is formed by stitching a first number of sub-medical images, the first number being greater than or equal to 2;

a display apparatus used to display a graphical user interface including a parameter configuration display window, wherein the parameter configuration display window simultaneously displays an exposure parameter for each of the first number of sub-medical images; and a control apparatus used to perform exposure according to an exposure parameter for each of the first number of sub-medical images, and to generate the medical image by performing stitching according to the first number of sub-medical images after the exposure, wherein the parameter configuration display window is configured to present the exposure parameters in association with the corresponding first number of sub-medical images, wherein the parameter configuration display window enables visual comparison of exposure parameters across the sub-medical images based on at least one of:

(i) a relative position of the sub-medical images, or (ii) an exposure sequence of the sub-medical images.

2. The medical imaging system of claim 1, wherein the parameter configuration display window includes a parameter list having a first number of rows, and wherein each of the first number of rows includes a sequence number corresponding to one of the first number of sub-medical images and an exposure parameter for the one of the first number of sub-medical images, and wherein the sequence number corresponds to an order of exposure for the first number of sub-medical images.

3. The medical imaging system of claim 1, further comprising:

an input apparatus used to receive a second input operation for adjusting exposure parameters for a second number of sub-medical images among the first number of sub-medical images, the second number being greater than or equal to 1 and less than or equal to the first number, wherein the control apparatus performs exposure according to the exposure parameter after adjustment by the second input operation.

4. The medical imaging system of claim 3, wherein the input apparatus receives a first input operation for selecting the second number of sub-medical images.

5. The medical imaging system of claim 3, wherein when the second number is 1, an exposure parameter corresponding to one sub-medical image is adjusted, and the exposure parameter for the one sub-medical image displayed in the parameter configuration display window is updated in real time to the adjusted exposure parameter, and when the second number is greater than 1, the exposure parameters for the second number of sub-medical images are adjusted simultaneously, and the exposure parameters for the second number of sub-medical images displayed in the parameter configuration display window are updated in real time to the adjusted exposure parameters.

6. The medical imaging system of claim 5, wherein when the second number is 1, the second input operation is used to adjust an absolute value of the exposure parameter for the one sub-medical image, and when the second number is greater than 1, the second input operation is used to adjust relative change values of the exposure parameters for the second number of sub-medical images.

7. The medical imaging system of claim 1, wherein an initial value of the exposure parameter for each sub-medical image displayed in the parameter configuration display window is a default value, the default value being related to one or more of the following: an anatomical location to be imaged, a size of the subject under examination, a distance from the X-ray source to the detector, a field of view of the imaging apparatus, an automatic exposure control ionization chamber mode, a focal spot size, and a configuration of a grid.

8. The medical imaging system of claim 3, wherein the graphical user interface includes an exposure parameter reset marker, and when the input apparatus receives a third input operation for triggering the exposure parameter reset marker, the exposure parameters for the first number of sub-medical images displayed in the parameter configuration display window are all updated to default values.

9. The medical imaging system of claim 3, wherein after the adjustment by the second input operation, when there is an exposure parameter that exceeds an upper limit value or that is less than a lower limit value, the exposure parameter displayed in the parameter configuration display window is updated to the upper limit value or the lower limit value.

10. The medical imaging system of claim 9, wherein the graphical user interface includes a focal spot adjustment marker, and when the input apparatus receives a fourth input operation for triggering the focal spot adjustment marker, the upper limit value or the lower limit value is adjusted to an upper limit value or lower limit value corresponding to an adjusted focal spot; and when there is an exposure parameter that exceeds the adjusted upper limit value or that is less than the adjusted lower limit value in the parameter configuration display window, the exposure parameter displayed in the parameter configuration display window is updated to the adjusted upper limit value or the adjusted lower limit value.

11. The medical imaging system of claim 3, further comprising an image capture apparatus used to capture the subject under examination to obtain a captured image including the subject under examination, and wherein the graphical user interface includes a region displaying the captured image, and markers for switch states of a plurality of automatic exposure control ionization chambers corresponding to the second number of sub-medical images superimposed and displayed on the captured image, and the states of the automatic exposure control ionization chambers corresponding to the second number of sub-medical images are set as ON or OFF by triggering the markers for the switch states, and wherein the states of the automatic exposure control ionization chambers corresponding to each sub-medical image are simultaneously displayed in the parameter configuration display window.

12. The medical imaging system of claim 1, wherein when the control apparatus performs exposure on one of the first number of sub-medical images, the exposure parameter for the one of the first number of sub-medical images displayed in the parameter configuration display window is an exposure parameter used in a current exposure, and the exposure parameter for the one of the first number of sub-medical images has a different display means from exposure parameters for other sub-medical images.

13. The medical imaging system of claim 1, wherein the graphical user interface includes a distance information display window for filling in or adjusting or displaying a distance between a center of a region of interest and a detector plane.

14. The medical imaging system of claim 1, wherein the exposure parameter includes at least one among a tube voltage, a tube current, a milliamp second, an exposure time, and an automatic exposure control ionization chamber.

15. A medical imaging system comprising:

a display apparatus used to display a graphical user interface including a parameter configuration window, wherein the parameter configuration window simultaneously displays an exposure parameter for each sub-medical image of a first number of sub-medical images, wherein a medical image of a subject under examination is formed by stitching the first number of sub-medical images, the first number being greater than or equal to 2, and wherein the parameter configuration display window includes a parameter list indicating a sequence number corresponding to one of the sub-medical images and an exposure parameter for the sub-medical images, and wherein the sequence number corresponds to an order of exposure for the sub-medical images.

16. The medical imaging system of claim 15, wherein the graphical user interface includes an exposure parameter reset marker, and when the exposure parameter reset marker is triggered, exposure parameters for the first number of sub-medical images displayed in the parameter configuration display window are all updated to default values, or exposure parameters for a second number of sub-medical images displayed in the parameter configuration display window are all updated to default values, the second number being greater than or equal to 1 and less than or equal to the first number.

17. The medical imaging system of claim 15, wherein the graphical user interface includes a region displaying a captured image, and markers for switch states of a plurality of automatic exposure control ionization chambers corresponding to a second number of sub-medical images superimposed and displayed on the captured image, and the states of the automatic exposure control ionization chambers corresponding to the second number of sub-medical images are set as ON or OFF by triggering the markers for the switch states, the second number being greater than or equal to 1 and less than or equal to the first number;

and the states of the automatic exposure control ionization chambers corresponding to each sub-medical image are simultaneously displayed in the parameter configuration display window.

18. A medical imaging method, the method comprising:

displaying a graphical user interface including a parameter configuration display window, wherein the parameter configuration display window simultaneously displays an exposure parameter for each sub-medical image of a first number of sub-medical images, and wherein a medical image of a subject under examination is formed by stitching the first number of sub-medical images, the first number being greater than or equal to 2, wherein the graphical user interface includes a distance information display window for filling in or adjusting or displaying a distance between a center of a region of interest and a detector plane; and performing exposure according to the exposure parameter for each sub-medical image, and generating the medical image by performing stitching according to the first number of sub-medical images after the exposure.

19. The method of claim 18, further comprising:

receiving a second input operation for adjusting exposure parameters for a second number of sub-medical images among the first number of sub-medical images, the second number being greater than or equal to 1 and less than or equal to the first number; and performing exposure according to the exposure parameter for each sub-medical image after adjustment by the second input operation.

20. The method of claim 19, further comprising receiving a first input operation for selecting the second number of sub-medical images.

* * * * *